(12) United States Patent
Church et al.

(10) Patent No.: US 9,387,050 B2
(45) Date of Patent: Jul. 12, 2016

(54) SURGICAL SYSTEM HAVING DETACHABLE COMPONENT AND STATE DETECTION CIRCUIT FOR DETECTION OF STATE OF ATTACHMENT OF DETACHABLE COMPONENT

(71) Applicant: GYRUS ACMI INC., Southborough, MA (US)

(72) Inventors: David C. Church, Millington, TN (US); Vlad Bluvshtein, Plymouth, MN (US); Lori Lucke, Rosemount, MN (US)

(73) Assignee: GYRUS ACMI INC., Southborough, MA (US)

( * ) Notice: Subject to any disclaimer, the term of this patent is extended or adjusted under 35 U.S.C. 154(b) by 0 days.

(21) Appl. No.: 14/486,368

(22) Filed: Sep. 15, 2014

(65) Prior Publication Data

US 2016/0074132 A1  Mar. 17, 2016

(51) Int. Cl.
*A61B 18/12* (2006.01)
*A61B 19/00* (2006.01)
*A61B 17/32* (2006.01)
*A61B 17/00* (2006.01)

(52) U.S. Cl.
CPC ......... *A61B 19/56* (2013.01); *A61B 17/320068* (2013.01); *A61B 18/1206* (2013.01); *A61B 2017/00017* (2013.01); *A61B 2017/00137* (2013.01); *A61B 2017/00464* (2013.01)

(58) Field of Classification Search
CPC ........... A61B 2018/00642; A61B 2018/00702; A61B 2018/00988; A61B 18/1206
See application file for complete search history.

(56) References Cited

U.S. PATENT DOCUMENTS

| | | |
|---|---|---|
| 3,223,088 A | 12/1965 | Barber et al. |
| 3,955,284 A | 5/1976 | Balson |
| 4,014,342 A | 3/1977 | Staub et al. |
| 4,878,493 A | 11/1989 | Pasternak et al. |
| 5,112,299 A | 5/1992 | Pascaloff |
| 5,230,704 A | 7/1993 | Moberg et al. |
| 5,275,609 A | 1/1994 | Pingleton et al. |

(Continued)

FOREIGN PATENT DOCUMENTS

| | | |
|---|---|---|
| EP | 1 201 196 A1 | 5/2002 |
| EP | 2 044 893 A2 | 4/2009 |

(Continued)

OTHER PUBLICATIONS

International Search Report and Written Opinion dated Jul. 23, 2015 from related International Application No. PCT/US2014/055611.

(Continued)

*Primary Examiner* — Jaymi Della
(74) *Attorney, Agent, or Firm* — Scully, Scott, Murphy & Presser, P.C.

(57) ABSTRACT

A surgical system and a method of providing and enabling a surgical system. The surgical system having a console and a first component configured to be directly or indirectly detachably attached to the console. The surgical system having a sensor circuit arranged to the console, and a first target state identifying circuit arranged to the first component. The sensor circuit outputs a feedback signal indicative of a state of electrical connection of the first target state identifying circuit to the sensor circuit. A controller arranged in the console is configured to control a therapy signal generator based on the feedback signal.

18 Claims, 4 Drawing Sheets

(56) References Cited

U.S. PATENT DOCUMENTS

| | | | |
|---|---|---|---|
| 5,352,222 A | 10/1994 | Rydell | |
| 5,376,078 A | 12/1994 | Dinger, III et al. | |
| 5,383,874 A * | 1/1995 | Jackson | A61B 18/00 606/1 |
| 5,395,312 A | 3/1995 | Desai | |
| 5,405,348 A | 4/1995 | Anspach, Jr. et al. | |
| 5,413,556 A | 5/1995 | Whittingham | |
| 5,492,527 A | 2/1996 | Glowa et al. | |
| 5,540,708 A | 7/1996 | Lim et al. | |
| 5,560,373 A | 10/1996 | DeSantis | |
| 5,569,254 A | 10/1996 | Carlson et al. | |
| 5,609,573 A | 3/1997 | Sandok | |
| 5,620,415 A | 4/1997 | Lucey et al. | |
| 5,620,447 A | 4/1997 | Smith et al. | |
| 5,712,543 A | 1/1998 | Sjostrom | |
| 5,792,167 A | 8/1998 | Kablik et al. | |
| 5,810,809 A | 9/1998 | Rydell | |
| 5,814,044 A | 9/1998 | Hooven | |
| 5,849,023 A | 12/1998 | Mericle | |
| 5,873,886 A | 2/1999 | Larsen et al. | |
| 5,899,915 A | 5/1999 | Saadat | |
| 5,904,681 A | 5/1999 | West, Jr. | |
| 6,042,593 A | 3/2000 | Storz et al. | |
| 6,053,923 A | 4/2000 | Veca et al. | |
| 6,074,386 A * | 6/2000 | Goble | A61B 18/1206 606/34 |
| 6,152,941 A | 11/2000 | Himes et al. | |
| 6,217,598 B1 | 4/2001 | Berman et al. | |
| 6,221,088 B1 | 4/2001 | Bays | |
| 6,246,638 B1 | 6/2001 | Zook et al. | |
| 6,293,957 B1 | 9/2001 | Peters et al. | |
| 6,296,638 B1 | 10/2001 | Davison et al. | |
| 6,454,782 B1 | 9/2002 | Schwemberger | |
| 6,494,892 B1 | 12/2002 | Ireland et al. | |
| 6,716,215 B1 | 4/2004 | David et al. | |
| 6,824,550 B1 | 11/2004 | Noriega et al. | |
| 2003/0165794 A1 * | 9/2003 | Matoba | A61B 19/44 433/114 |
| 2004/0010258 A1 | 1/2004 | Carusillo et al. | |
| 2004/0147947 A1 * | 7/2004 | Donofrio | A61B 17/320068 606/169 |
| 2004/0167427 A1 | 8/2004 | Quick et al. | |
| 2006/0074405 A1 | 4/2006 | Malackowski et al. | |
| 2009/0275940 A1 * | 11/2009 | Malackowski | A61B 18/1442 606/42 |
| 2010/0317998 A1 | 12/2010 | Hibner et al. | |
| 2011/0017801 A1 | 1/2011 | Zemlok et al. | |
| 2011/0066142 A1 | 3/2011 | Tal et al. | |
| 2012/0098609 A1 | 4/2012 | Verma et al. | |
| 2014/0155888 A1 | 6/2014 | Edwards et al. | |

FOREIGN PATENT DOCUMENTS

| | | |
|---|---|---|
| EP | 2 133 028 A2 | 12/2009 |
| GB | 2470607 A | 12/2010 |
| WO | 2014/101943 A1 | 7/2014 |

OTHER PUBLICATIONS

International Search Report and Written Opinion dated Mar. 25, 2014 from International Application No. PCT/US2013/077758.

* cited by examiner

SURGICAL SYSTEM HAVING DETACHABLE COMPONENT AND STATE DETECTION CIRCUIT FOR DETECTION OF STATE OF ATTACHMENT OF DETACHABLE COMPONENT

BACKGROUND

The invention relates generally to a surgical system including a console and a replaceable component that is directly or indirectly attached to the console, and a method of providing the surgical system.

The invention further relates to detection of one or more states of electrical arrangement of the replaceable component and control of one or more therapeutic functions of the replaceable component based on the detected one or more states.

BRIEF SUMMARY

In accordance with a first embodiment, a surgical system is provided. The surgical system comprises: a console comprising: an electrical isolation device; a therapy signal generator configured to generate a therapy signal; and a controller configured to control the therapy signal generator; a first component configured to be directly or indirectly detachably attached to the console, wherein the first component is configured to be driven by the therapy signal to therapeutically affect a biological tissue; a sensor circuit arranged to the console, the sensor circuit comprising: a device state signal generation circuit configured to generate a device state signal; and a reference circuit configured provide a baseline signal based on the device state signal; and a first target state identifying circuit arranged to the first component, wherein the first target state identifying circuit is configured to be selectively electrically connected in a first connected state to the sensor circuit, and wherein in the first connected state, the first target state identifying circuit is configured to provide a first target state identifying signal based on the device state signal; wherein the sensor circuit is configured to output a feedback signal based on the baseline signal and the first target state identifying signal through the electrical isolation device, and wherein the controller is configured to control the therapy signal generator based on the feedback signal.

In accordance with a second embodiment, a surgical system is provided. The surgical system comprises: a console comprising: an electrical isolation device; a therapy signal generator configured to generate a therapy signal; and a controller configured to control the therapy signal generator, wherein the console is configured to be directly or indirectly detachably attached to a first component, wherein the first component is configured to be driven by the therapy signal to therapeutically affect a biological tissue; and a sensor circuit arranged to the console, the sensor circuit comprising: a device state signal generation circuit configured to generate a device state signal; and a reference circuit configured to provide a baseline signal based on the device state signal, wherein the sensor circuit is configured to be selectively electrically connected in a first connected state to a first target state identifying circuit arranged to the first component, and wherein in the first connected state, the first target state identifying circuit is configured to provide a first target state identifying signal based on the device state signal, wherein the sensor circuit is configured to output a feedback signal based on the baseline signal and the first target state identifying signal through the electrical isolation device, and wherein the controller is configured to control the therapy signal generator based on the feedback signal.

In accordance with a third embodiment, a method of providing a surgical system is provided. The method comprises: providing a console comprising: an electrical isolation device; a therapy signal generator configured to generate a therapy signal; and a controller configured to control the therapy signal generator; providing a first component configured to be directly or indirectly detachably attached to the console, wherein the first component is configured to be driven by the therapy signal to therapeutically affect a biological tissue; providing a sensor circuit arranged to the console, the sensor circuit comprising: a device state signal generation circuit configured to generate a device state signal; and a reference circuit configured provide a baseline signal based on the device state signal; providing a first target state identifying circuit arranged to the first component, wherein the first target state identifying circuit is configured to be selectively electrically connected in a first connected state to the sensor circuit, and wherein in the first connected state, the first target state identifying circuit is configured to provide a first target state identifying signal based on the device state signal, enabling the sensor circuit to output a feedback signal based on the baseline signal and the first target state identifying signal, and enabling the controller to control the therapy signal generator based on the feedback signal.

BRIEF DESCRIPTION OF THE DRAWING

These and other features, aspects, and advantages of the present invention will become better understood when the following detailed description is read with reference to the accompanying drawings in which like characters represent like parts throughout the drawings, wherein.

DETAILED DESCRIPTION

Figure 1:
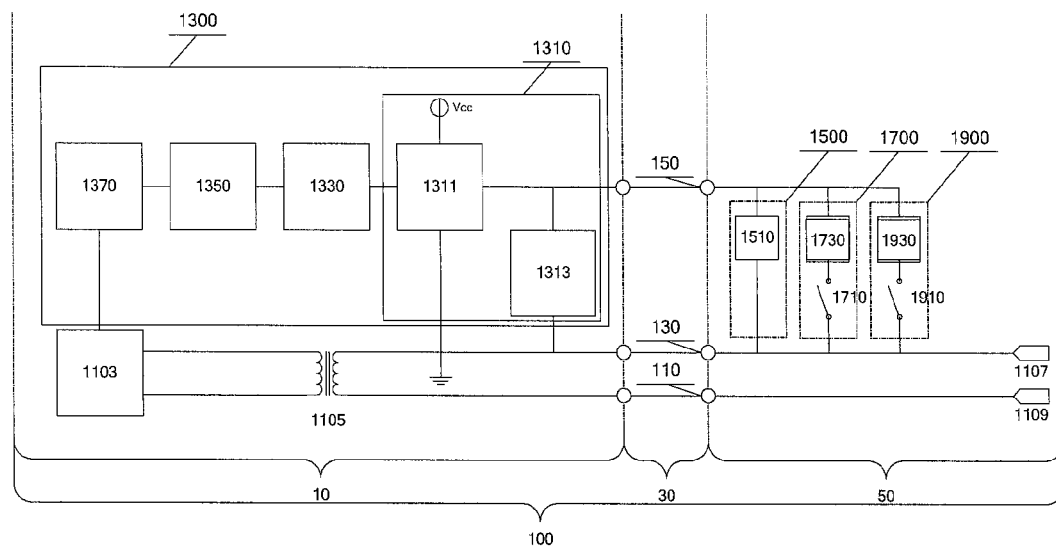
FIG. 1 is a diagram showing a surgical system in accordance with a first embodiment of the invention.

In one embodiment illustrated in FIG. 1, a surgical system 1 includes a console 10, an intermediate component 30 that is detachably attachable to the console 10, and a first component 50 that is detachably attachable to the intermediate component 30.

An example of the intermediate component 30 is a handpiece. An example of the first component 50 is an interchangeable tip that is configured to be detachably attached to the handpiece. Additional detailed descriptions of exemplary structures of the console 10, the intermediate component 30, and the first component 50 will be discussed further below.

The surgical system 1 further includes a circuit 100 that is distributively arranged to the console 10, the intermediate component 30, and the first component 50.

The circuit 100 includes an alternating current (AC) signal generator 1103, a step-up transformer 1105, a pair of electrical leads 1107, 1109, a target state detection circuit 1300 including a sensor circuit 1310, a first target state identification circuit 1500, and a second target state identification circuit 1700.

As illustrated in FIG. 1, the AC signal generator 1103, the step-up transformer 1105 and the target state detection circuit 1300 are arranged in the console 10, the first target state identification circuit 1500 and the second target state identification circuit 1700 are arranged in the first component 50, and the pair of electrical leads 1107, 1109 are arranged across the console 10, the intermediate component 30, and the first component 50.

The AC signal generator 1103 provides a time varying signal (and more specifically, an AC signal, to a low voltage side of the step-up transformer 1105. The step-up transformer 1105 steps up a voltage of the AC signal to a high voltage, and outputs the high voltage AC signal on a high voltage side of the step-up transformer 1105 to the pair of electrical leads 1107, 1109. The high voltage AC signal is characterized by at least one of a frequency and a voltage that is desirable for one or more therapeutic functions performed by the first component. Examples of the one or more therapeutic functions performed by the first component will be described in further detail below. The high voltage AC signal is referred to herein as a "therapy signal." The therapy signal may range, for example, from about 150 V to about 1500 V, with frequencies ranging from about 10 kHz to about 500 kHz.

In a modification of the surgical system 1, the AC signal generator 1103 and the step-up transformer 1105 can be replaced with a signal generator configured to generate a therapy signal that is characterized by at least one of a frequency and a voltage that is desirable for one or more therapeutic functions performed by the first component.

The sensor circuit 1310 is configured to detect one or more states of electrical arrangement of the first component 50 to the console 10 via the intermediate component 30. In a first arrangement, the first component 50 is not attached to the intermediate component 30. In a second arrangement, the first component 50 is attached to the console via the intermediate component 30. In a third arrangement, the first component 50 is attached to the console 10 via the intermediate component 30 and a switch provided to the first component 50 is actuated by a user.

The target state detection circuit 1300 includes the sensor circuit 1310. The sensor circuit 1310 includes a device state signal generation circuit 1311 and a reference circuit 1313. The device state signal generation circuit 1311 provides a device state signal that is referenced to one of the electrical leads 1107, 1109.

In the first arrangement, the reference circuit 1313 is electrically connected to the device state signal generation circuit 1311 to provide a baseline signal based on the device state signal.

In the second arrangement, the reference circuit 1313 and the first target state identification circuit 1500 are electrically connected to the device state signal generation circuit 1311. Specifically, the first target state identification circuit 1500 is electrically connected to the device state signal generation circuit 1311 upon physical attachment of the first component 50 to the intermediate component 30 and upon physical attachment of the intermediate component 30 to the console 10. In the second arrangement, the reference circuit 1313 and the first target state identification circuit 1500 provide the baseline signal and a first target state identification signal based on the device state signal.

In the third arrangement, the reference circuit 1313, the first target state identification circuit 1500, and the second target state identification circuit 1700 are electrically connected to the device state signal generation circuit 1311. The first target state identification circuit 1500 is electrically connected to the device state signal generation circuit 1311 upon physical attachment of the first component 50 to the intermediate component 30 and upon physical attachment of the intermediate component 30 to the console 10.

The second target state identification circuit 1700 includes a second target state identification circuit switch 1710 that is actuated by a user. The second target state identification circuit 1700 is electrically connected to the device state signal generation circuit 1311 upon physical attachment of the first component 50 to the intermediate component 30, physical attachment of the intermediate component 30 to the console 10 and actuation of the second target state identification circuit switch 1710 by the user.

In the third arrangement, the reference circuit 1313, the first target state identification circuit 1500, and the second target state identification circuit provide the baseline signal, the first target state identification signal, and a second target state identification signal based on the device state signal.

The target state detection circuit 1300 further includes an analog to digital convertor (ADC) 1330, an electrical isolation circuit 1350 and a controller 1370. The ADC 1330 is configured to convert a characteristic of the baseline signal, the first target state identifying signal and the second target state identifying signal to a digital signal. The digital signal is then passed through the electrical isolation circuit 1350 as a low voltage signal to the controller 1370 as feedback data. Examples of the electrical isolation circuit 1350 include an opto-isolator, a capacitive isolator, and an inductive isolator.

The controller 1370 is configured to control at least one therapeutic function performed by the first component 50 based on the feedback data.

In one example, the controller 1370 is implemented by hardware or a combination of hardware and software. The controller 1370 is configured to correlate the characteristic of the baseline signal, the first target state identification signal, and the second target state identification signal with one or more predetermined values in a look-up table. Based on the one or more predetermined values, the controller 1370 is configured to determine, for example, one or more of the following states of electrical arrangement of the first component 50: the first component 50 is not attached to the console 10, the first component 50 is attached to the console 10 and is a recognized component or one of a set of recognized components, the first component 50 is attached to the console 10 and is not a recognized component, a switch of a recognized component is activated, and the switch of the recognized component is not activated. The controller 1370 is further configured to control one or more therapeutic functions performed by the first component 50 based on the determined one or more states of electrical arrangement of the first component 50.

The surgical system 1 is not limited to a first target state identification circuit 1500 and a first target state identification circuit 1700. The surgical system 1 can include a third target state identification circuit 1900 and additional target state identification circuits that can be arranged to be electrical connected to the device state signal generation circuit. The third target state identification circuits can include a third target state switch 1910 that is actuated by the user to electrically connect the third target state identification circuit to the device state signal generation circuit 1311. The third and additional target state identification circuit are configured to provide a third and additional target state identification signals, the characteristics of which can be correlated by the controller 1370 with predetermined values in the look-up table. Based on the predetermined values, the controller 1370 is configured to determine additional states of electrical arrangement of the first component 50. The controller is configured to control additional therapeutic functions performed by the first component based on the determined additional states of electrical arrangement of the first component 50.

Examples of the sensor circuit 1310, the first target state identification circuit 1500 and the first target state identification circuit 1700 are discussed below.

The sensor circuit 1310, the first target state identification circuit 1500, the first target state identification circuit 1700, and the third target state identification circuit 1900 can be implemented by, for example, an astable oscillator circuit (or more generally, a capacitive sensing circuit).

Figure 3:
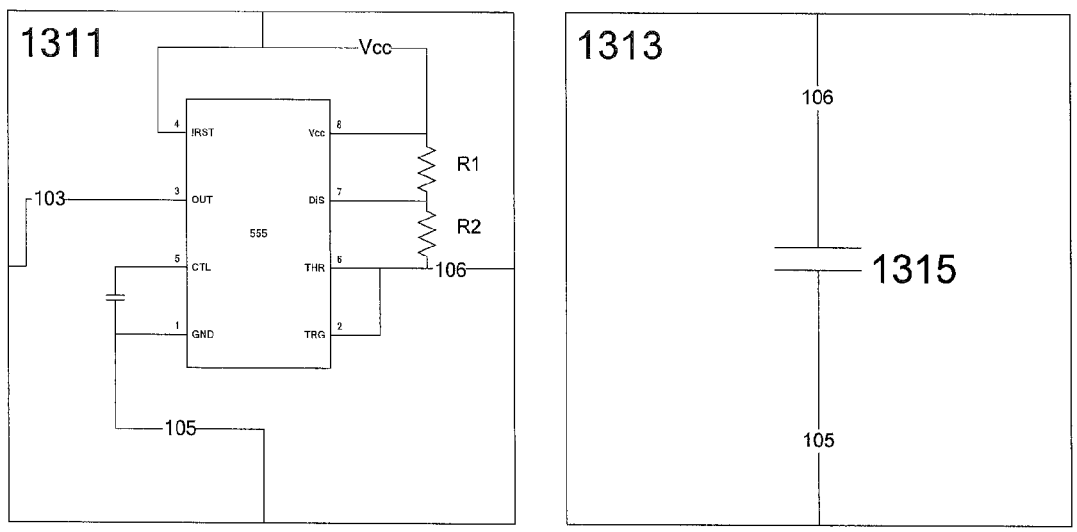
FIG. 3 is a diagram showing an example of the surgical system illustrated in FIG. 1 wherein a target state detection circuit and three target state identification circuits are implemented as an astable oscillator circuit.
Figure 3:
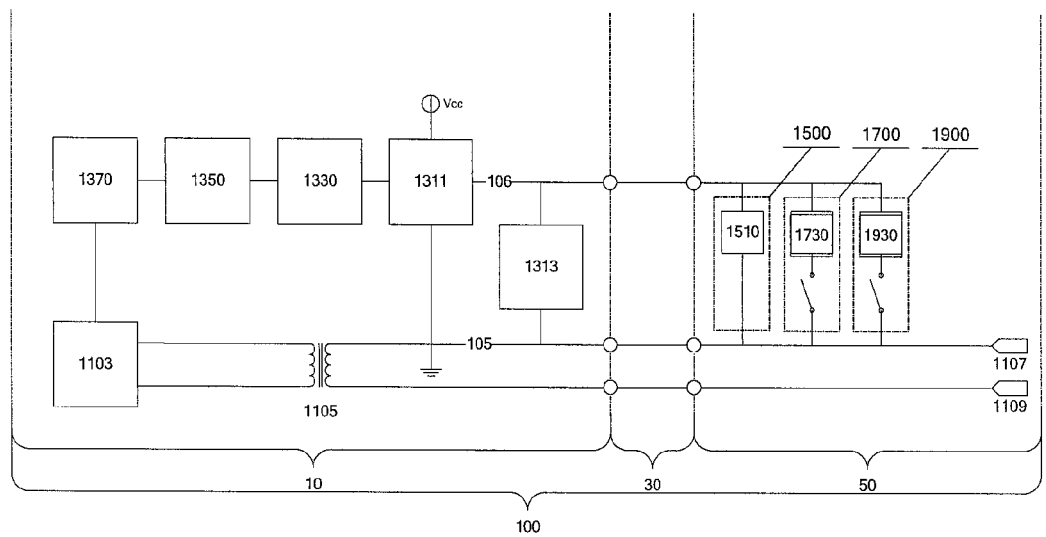

FIG. 3 illustrates an example of an astable oscillator circuit implemented with a 555 timer integrated circuit. The frequency of the astable oscillator output signal is controlled by the fixed electrical connection to the reference circuit 1313 (including the reference capacitor 1315) and (i) the selective electrical connection of the first target state identification circuit 1500 (including a first target state capacitor 1510) upon physical attachment of the first component 50 to the console 10 via the intermediate component 30, (ii) the selective electrical connection of the second target state identification circuit 1700 (including a second target state capacitor 1730 and a second target state switch) upon the actuation of the second target state switch 1710 by the user, and (iii) the selective electrical connection of the third target state identification circuit 1900 (including a third target state capacitor 1930 and a third target state switch 1910) upon the actuation of the third target state switch 1910 by the user. The astable oscillator's output signal frequency is indirectly proportional to the capacitance offered by the reference capacitor, the first target capacitor 1510, the second target capacitor 1730 and the third target capacitor 1930.

In FIG. 3, the trigger pin (2) and the threshold pin (6) are connected so as to form a self-trigger, causing the 555 timer IC to operate as an astable oscillator. Here resistor R1 and resistor R2 act as timing resistors and the discharge pin (7) is connected to the junction of resistor R1 and resistor R2. When the supply Vcc is connected, the reference capacitor 1315, and the selectively electrically connected first target capacitor 1510, second target capacitor 1730, and third target capacitor 1930 act like a timing capacitor and change toward Vcc. When the one or more capacitors get charged, the output pin (3) is held high. When the one or more capacitors voltage is just greater than (⅔) Vcc, the upper comparator of the 555 timer IC triggers the internal control flip flop and the one or more capacitors discharge towards the ground through resistor R2. During this discharge cycle the output is held low. During this discharge, as the voltage across the one or more capacitors reaches (⅓) Vcc the lower comparator is triggered and again it starts charging and the output is held high.

As additional capacitors are electrically connected, the offered capacitance increases, thereby decreasing the frequency of the astable oscillator output. Based on the predetermined ratings of the reference capacitor, the first target capacitor, the second target capacitor, and the third target capacitor, the frequency of the astable oscillator output can be correlated utilized to determine one or more states of electrical arrangement of the first component.

The output of the astable oscillator from pin 3 is referred to herein as a feedback signal. The feedback signal can be a square wave. In the above-described first arrangement where the first component is not attached to the console, the reference capacitor 1315 is selected such that the astable oscillator provides a feedback signal having a measurable baseline frequency. In the above-described second arrangement where the first component 50 is attached to the console 10, the first target state capacitor 1510 is selected such that the astable oscillator provides a feedback signal having a measurable first frequency that is different from the baseline frequency. In the above-described third arrangement where the first component 50 is attached to the console 10 and the second target switch 1710 is actuated to electrically connect the second target state capacitor 1730, the second target state capacitor 1730 is selected such that the astable oscillator provides a feedback signal having a measurable second frequency that is different from the baseline frequency and the first frequency. The controller 1370 is then configured to determine the capacitance provided in the astable oscillator by, for example, counting the pulses of the square wave in a predetermined time period. The determined capacitance then indicates the state of electrical arrangement of the first component 50 to the console 10. It is noted that even in the absence of an attachment of the first component 50 to the console 10 (i.e. the above-described first arrangement), the surgical system 1 and in particular the circuit 100 provides for the reference circuit 1313 including the reference capacitor 1315 in the console 10 such that the feedback signal based on the baseline frequency is provided to the controller 1370 to control the AC signal generator 1103.

In a modification of the circuit 100 shown in FIG. 3, the astable oscillator circuit configured using a 555 timer IC can be implemented by replacing the reference capacitor 1315 with a reference resistor, and replacing the one or more of the first target capacitor 1510, the second target capacitor 1730, and the third target capacitor with a corresponding one or more of a first target resistor, a second target resistor, and a third target resistor.

Figure 4:
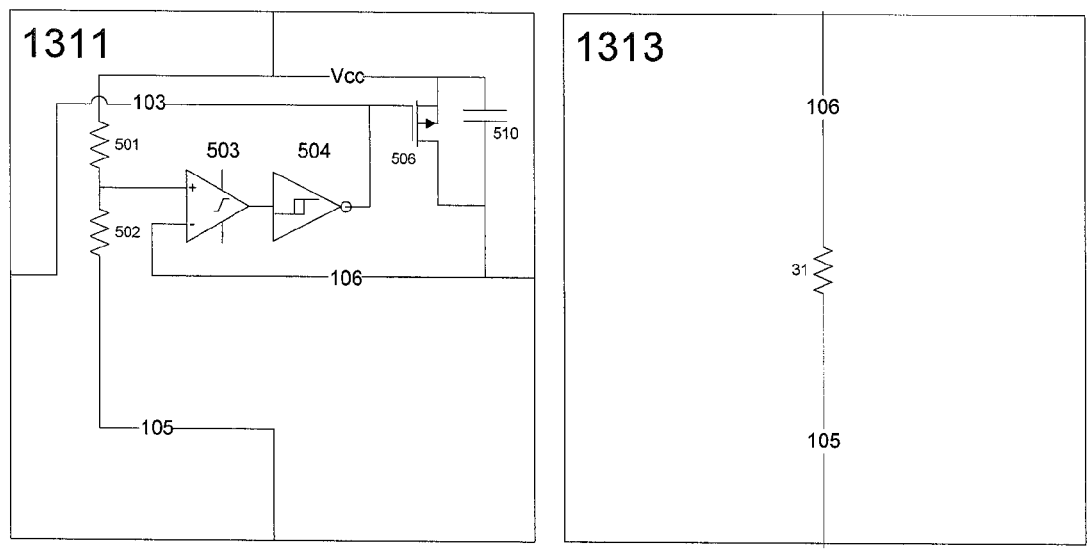
FIG. 4 is a diagram showing an example of the surgical system illustrated in FIG. 1 wherein a target state detection circuit and three target state identification circuits are implemented as an astable oscillator circuit.
Figure 4:
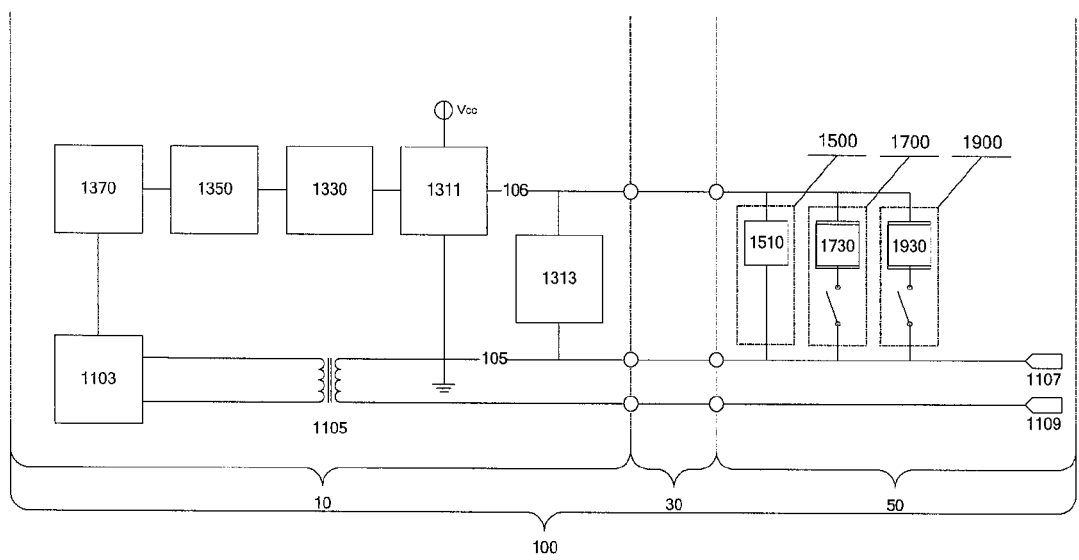

FIG. 4 illustrates another example of an astable oscillator circuit and a reference circuit that implements the sensor circuit 1310.

FIG. 4 shows an astable oscillator as a relaxation oscillator. A comparator takes in and compares a reference voltage from a voltage divider and the device state signal, and sends the output to a resetting latch which provides feedback to the comparator to provide the feedback signal to the controller. The resetting latch is comprised of a Schmidt trigger to provide hysteresis and a transistor switch to reset the oscillation.

In FIG. 4, a reference resistor 1315, a first target resistor 1510, a second target resistor 1730, and a third target resistor 1930 replaces the reference capacitor 1315, the first target capacitor 1510, the second target capacitor 1730, and the third target capacitor 1930 respectively described above with respect to FIG. 3.

Figure 5:
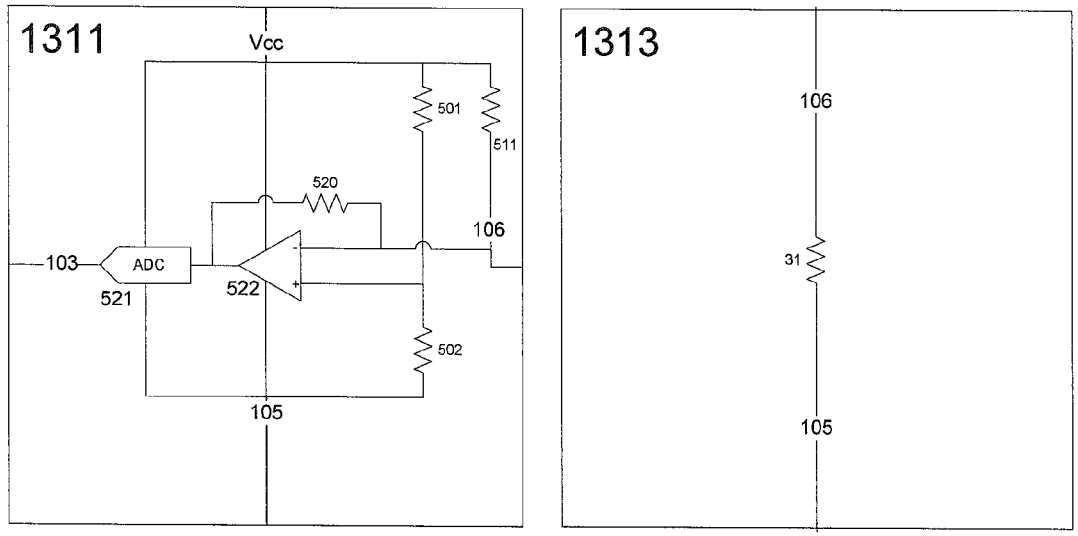
FIG. 5 is a diagram showing an example of the surgical system illustrated in FIG. 1 wherein a target state detection circuit and three target state identification circuits are implemented as an voltage sensor.
Figure 5:
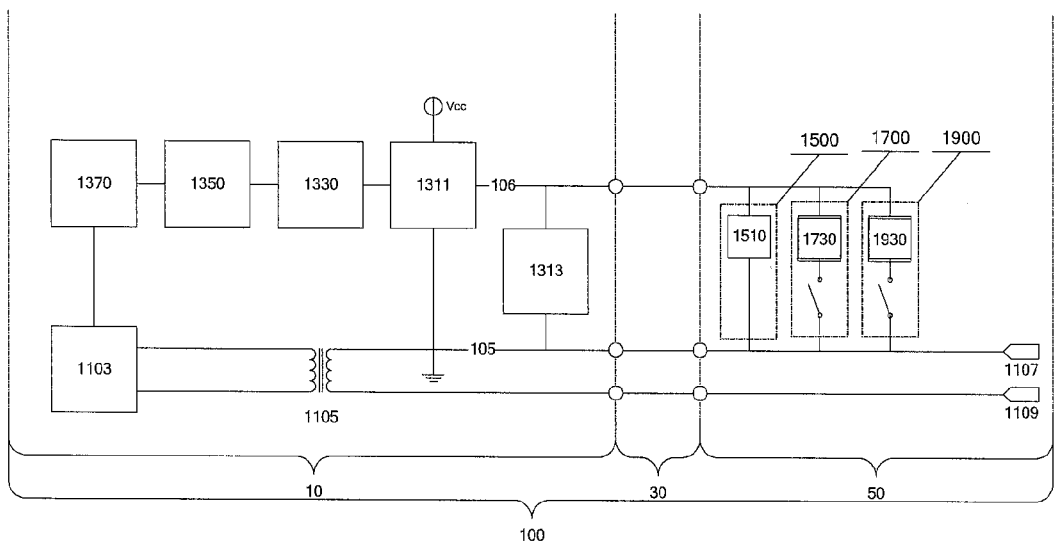

The sensor circuit 1310, the first target state identification circuit 1500, the first target state identification circuit 1700, and the third target state identification circuit 1900 can also be implemented by, for example, an a voltage sensor as illustrated in FIG. 5.

FIG. 5 shows a device state signal sensing circuit for DC, non-time varying signals. A supply voltage is supplied to the reference resistor 1510 and the one or more target resistors by the supply Vcc through a pull up resistor 511 on bus 106. The device state signal voltage on bus 106 is compared by device 522 to a reference voltage supplied by the voltage divider comprised of resistors 501 and 502. Stability of the comparison is provided by a feedback resistor 520. The output of the comparator 522 is provided to an analog to digital converter 521 to create the feedback signal.

A more detailed description of the exemplary structures of the surgical system 1 will be discussed below. Examples of interchangeable tips that make up the first component and a handpiece that makes up the intermediate will be described below.

In a first example, a handpiece and a debrider blade as an interchangeable tip that is detachably attachable to the handpiece are provided. Detailed descriptions of the structures of the handpiece and the debrider blade can be found at, for example, U.S. patent application Ser. No. 13/803,380, the contents of which are incorporated herein by reference.

The debrider blade can include a first (outer) tubular body and a second (inner) tubular body. The second tubular body is at least partially disposed within the first tubular body, and is arranged to be moved by rotation or reciprocation with respect to the first tubular body.

In the first example, a motor (or more generally, a power transfer device) that is suitable to move the second tubular body to rotate or reciprocate is arranged in the handpiece or in the interchangeable tip. The motor is in turn driven by a signal generator arranged in the console.

The first tubular body can include a first set of teeth arranged at an opening of the first tubular body. The second tubular body can include a second set of teeth arranged at an opening of the second tubular body. As the second tubular body is moved by rotation or reciprocation, a tissue that is arranged between the first set of teeth and the second set of teeth is sheared or dissected by the rotational or reciprocal movement of the second set of teeth.

As an alternative to the first set of teeth and the second set of teeth, the first tubular body can be provided with a first opening and the second tubular body can be replaced with a rotatable burr that can be driven by the motor to rotate to remove a target tissue.

In the first example, the interchangeable tip is provided with the first target state identification circuit 1500 and the first target state identification circuit 1700 described above.

A second example of the interchangeable tip includes a modification of the first example of the interchangeable tip. In the second example, bipolar cauterization and/or coagulation functions are provided. Specifically, the first tubular body is charged with a first electrical potential (as an active electrode) and the second tubular body is charged with a second electrical potential (as a return electrode) that is different for the first electrical potential. The active electrode is electrically connected to the electrical lead 1107 and the return electrode is electrically connected to the electrical lead 1109.

Referring back to FIG. 1, the interchangeable tip according to the second example is electrically connected to the handpiece through three pins 110, 130 and 150. The therapy signal is provided into the interchangeable tip through pins 110, 130. The first through third target state identifying signal are provided from the interchangeable tip to the sensor circuit 110 through pins 130 and 150. In the target state detection circuit 1300, the electrical isolation device 1350 then separates the feedback signal output by the sensor circuit 1310 from the therapy signal and transfers the feedback signal to the controller 1370.

As an alternative to the bipolar configuration described above, a monopolar configuration can be provided. In the monopolar configuration, the first tubular body is charged with a first electrical potential (as an active electrode) and a return electrode (as a second component) separate from the interchangeable tip is provided.

In the second example, the interchangeable tip is provided with the first target state identification circuit 1500 and the second target state identification circuit 1700, as described above, and a third target state identification circuit 1900 including a third target state identification switch 1910.

In an arrangement in which the third target state identification switch is actuated by the user, the controller may be configured to determine that the user has instructed a cauterization and/or coagulation function. Based on this determination, the controller 1370 may be configured to control the AC signal generator 1103 to enable cauterization and/or coagulation function.

The invention is not limited to the above-described examples. The invention also encompasses structures that can be driven to provide different combinations of the dissection, suction, and cauterization and/or coagulation functions described above.

The invention also encompasses, for example, an interchangeable tip that is configured to be controlled to perform other therapeutic functions such as dissection through ultrasonic vibrations. To enable dissection through ultrasonic vibrations, the first component can include a piezoelectric transducer and an end effector that is movably connected to the piezoelectric transducer. The piezoelectric transducer is electrically connected to electrical leads 1107, 1109 to be driven by the AC signal generator 1103.

Figure 2:
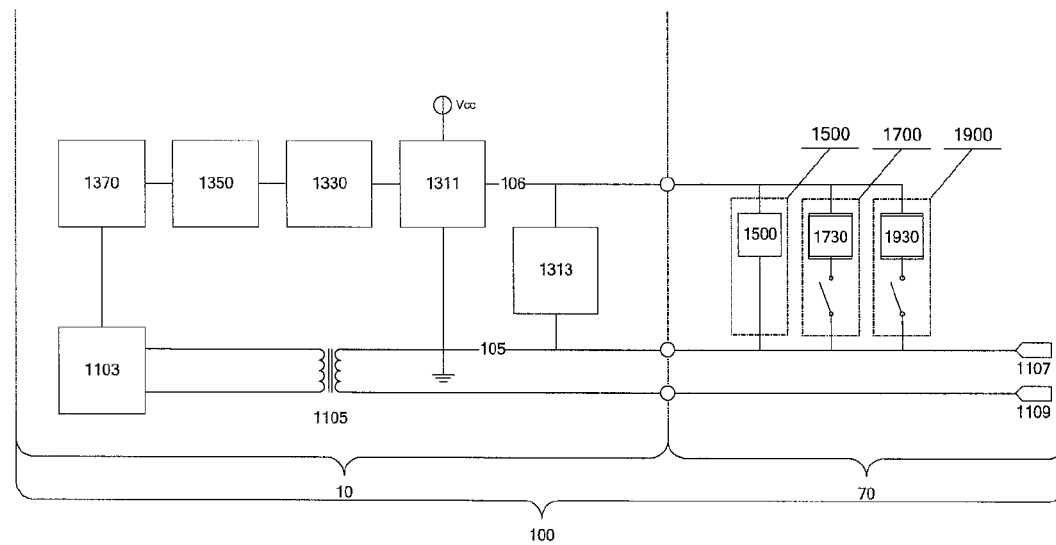
FIG. 2 is a diagram showing a modification of the surgical system illustrated in FIG. 1.

A modification of the above-described surgical system 1 is illustrated in FIG. 2. According to the modification of the surgical system 1, the above-described indirect attachment of the first component 50 to the console 10 via the intermediate component 30 is replaced by a direct attachment of a first component 70 to the console 10. Specifically, the first target state identification circuit 1500 and the second target state identification circuit 1700 are electrically connected to the device state signal generation circuit 1311 upon physical attachment of the first component 50 to the console 10.

In another embodiment, a method for detecting one or more states of electrical arrangement of a replaceable component and control of one or more therapeutic functions of the replaceable component based on the detected one or more states is provided.

The method includes a step of providing a console including the step-up transformer 1105, the AC signal generator 1103 (or more generally, a therapy signal generator) configured to generate a therapy signal through the step-up transformer 1105, and a controller 1370 configured to control the AC signal generator 1103 (or therapy signal generator). The method further includes a step of providing a first component 50 configured to be directly or indirectly detachably attached to the console 10, wherein the first component 50 is configured to be driven by the therapy signal to therapeutically affect a biological tissue. The method further includes a step of providing a sensor circuit 1310 arranged to the console 10, the sensor circuit including a device state signal generation circuit 1311 configured to generate a device state signal, and a reference circuit 1313 configured output a baseline signal based on the device state signal. The method further includes providing a first target state identification circuit 1500 arranged to the first component 50, wherein the first target state identification circuit 1500 is configured to be selectively electrically connected in a first connected state to the sensor circuit, and wherein in the first connected state, the first target state identification circuit 1500 is configured to output a first target state identification signal based on the device state signal. The method further includes a step of enabling the sensor circuit 1310 to output the baseline signal and the first target state identification signal through an electrical isolation circuit 1350 as feedback data, and a step of enabling the controller 1370 to control the AC signal generator 1103 (or the therapy signal generator) based on the feedback data. The method further includes providing a first target state identification circuit 1700 to the first component 50. The method further includes enabling the second target state identification circuit 1700 to be selectively electrically connected to the sensor circuit 1310 by the actuation of a second target state switch 1710, wherein the second target state identification circuit 1700 outputs a second target state identification signal based on the device state signal. The method further includes enabling sensor circuit 1310 to output the second target state identification signal through the electrical isolation circuit 1350 as feedback data, and a step of enabling the controller 1370 to control the AC signal generator 1103 (or the therapy signal generator) based on the feedback data. The method further includes enabling the controller 1370 to continuously or periodically control the AC signal generator 1103 (or the therapy signal generator) based on the feedback data.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

Furthermore, to the extent that the terms "includes," "has" or "having" or variations in form thereof are used in either the detailed description or the claims, such terms are intended to be inclusive in a manner similar to the term "comprising" as "comprising" is interpreted when employed as a transitional word in a claim.

The claimed invention is:

1. A surgical system comprising:
   a console comprising:
      an electrical isolation device;
      a therapy signal generator configured to generate a therapy signal; and
      a controller configured to control the therapy signal generator;
   a first component configured to be directly or indirectly detachably attached to the console, wherein the first component is configured to be driven by the therapy signal to therapeutically affect a biological tissue;
   a sensor circuit arranged to the console, the sensor circuit comprising:
      a device state signal generation circuit configured to generate a device state signal; and
      a reference circuit configured to provide a baseline signal based on the device state signal; and
   a first target state identifying circuit arranged to the first component,
      wherein the first target state identifying circuit is configured to be selectively electrically connected in a first connected state to the sensor circuit, and
      wherein in the first connected state, the first target state identifying circuit is configured to provide a first target state identifying signal based on the device state signal,
   wherein the sensor circuit is configured to output a feedback signal based on the baseline signal and the first target state identifying signal through the electrical isolation device, and
   wherein the controller is configured to control the therapy signal generator based on the feedback signal.

2. The surgical system according to claim 1,
   wherein the therapy signal generator is configured to generate the therapy signal as an AC signal, and to output the therapy signal to a pair of electrical leads,
   wherein the feedback signal has a direct electrical path to one of the pair of electrical leads, and
   wherein the electrical isolation device separates the feedback signal from the therapy signal and transfers the feedback signal to the controller.

3. The surgical system according to claim 1, wherein the sensor circuit is arranged as an astable oscillator circuit.

4. The surgical system according to claim 1, wherein the sensor circuit is arranged as a voltage sensor circuit.

5. The surgical system according to claim 1, wherein the sensor circuit and the first target state identifying circuit are arranged as a voltage sensor circuit.

6. The surgical system according to claim 1,
   wherein the reference circuit comprises a reference capacitor, and the first target state identifying circuit comprises a first target capacitor configured, in the first connected state, to be selectively electrically connected in parallel with the reference capacitor, or
   wherein the reference circuit comprises a reference resistor, and the first target state identifying circuit comprises a first target resistor configured, in the first connected state, to be selectively electrically connected in parallel with the reference resistor.

7. The surgical system according to claim 1,
   further comprising a second target state identifying circuit arranged to the first component and a second target switch,
   wherein the second target state identifying circuit is configured to be selectively electrically connected in a second connected state to the sensor circuit,
   wherein in the second connected state, the second target state identifying circuit is configured to provide a second target state identifying signal based on the device state signal,
   wherein the sensor circuit is further configured to output the feedback signal based on the baseline signal, the first target state identifying signal and the second target state identifying signal through the electrical isolation device, and
   wherein the controller is configured to control the therapy signal generator based on the feedback signal,
   wherein
      the reference circuit comprises a reference capacitor, the first target state identifying circuit comprises a first target capacitor configured, in the first connected state, to be selectively electrically connected in parallel with the reference capacitor, the second target state identifying circuit comprises a second target capacitor configured, in the second connected state, to be selectively electrically connected in parallel with the reference capacitor and the first target capacitor and the second target switch is configured to be controlled to electrically connect the second target capacitor in parallel with the reference capacitor, or
      the reference circuit comprises a reference resistor, the first target state identifying circuit comprises a first target resistor configured, in the first connected state, to be selectively connected in parallel with the reference resistor, the second target resistor configured in the second connected state, to be selectively electrically connected in parallel with the reference resistor and the first target resistor and the second target switch is configured to be controlled to electrically connect the second target resistor in parallel with the reference resistor.

8. The surgical system according to claim 1, wherein
the reference circuit comprises a reference capacitor and the first target state identifying circuit comprises a first target capacitor configured, in the first connected state, to be selectively electrically connected in parallel with the reference capacitor by attaching the first component to the console, or
the reference circuit comprises a reference resistor, the first target state identifying circuit comprises a first target resistor configured, in the first connected state, to be selectively connected in parallel with the reference resistor by attaching the first component to the console.

9. The surgical system according to claim 1, wherein in an absence of the first target state identifying signal, the baseline signal indicates that the first component is detached from the console.

10. The surgical system according to claim 1, wherein the first component is configured to be indirectly attached to the console via an intermediate component that is configured to be detachably attachable to the console.

11. A surgical system comprising:
a console comprising:
an electrical isolation device;
a therapy signal generator configured to generate a therapy signal; and
a controller configured to control the therapy signal generator,
wherein the console is configured to be directly or indirectly detachably attached to a first component, wherein the first component is configured to be driven by the therapy signal to therapeutically affect a biological tissue; and
a sensor circuit arranged to the console, the sensor circuit comprising:
a device state signal generation circuit configured to generate a device state signal; and
a reference circuit configured to provide a baseline signal based on the device state signal,
wherein the sensor circuit is configured to be selectively electrically connected in a first connected state to a first target state identifying circuit arranged to the first component, and
wherein in the first connected state, the first target state identifying circuit is configured to provide a first target state identifying signal based on the device state signal,
wherein the sensor circuit is configured to output a feedback signal based on the baseline signal and the first target state identifying signal through the electrical isolation device, and
wherein the controller is configured to control the therapy signal generator based on the feedback signal.

12. The surgical system according to claim 11, wherein the sensor circuit is arranged as an astable oscillator circuit.

13. The surgical system according to claim 11, wherein the sensor circuit is arranged as a voltage sensor circuit.

14. The surgical system according to claim 11, wherein
the reference circuit comprises a reference capacitor and the first target state identifying circuit comprises a first target capacitor configured, in the first connected state, to be selectively electrically connected in parallel with the reference capacitor, or
the reference circuit comprises a reference resistor and the first target state identifying circuit comprises a first target resistor configured, in the first connected state, to be selectively electrically connected in parallel with the reference resistor.

15. The surgical system according to claim 11, wherein the sensor circuit is further configured to be selectively electrically connected in a second connected state to a second target state identifying circuit arranged to the first component,
further comprising a second target switch,
wherein in the second connected state, the second target state identifying circuit is configured to provide a second target state identifying signal based on the device state signal,
wherein the sensor circuit is further configured to output the feedback signal based on the baseline signal, the first target state identifying signal and the second target state identifying signal through the electrical isolation device,
wherein the controller is configured to control the therapy signal generator based on the feedback signal, and
wherein
the reference circuit comprises a reference capacitor, the first target state identifying circuit comprises a first target capacitor configured, in the first connected state, to be selectively electrically connected in parallel with the reference capacitor, the second target state identifying circuit comprises a second target capacitor configured, in the second connected state, to be selectively electrically connected in parallel with the reference capacitor and the first target capacitor and the second target switch is configured to be controlled to electrically connect the second target capacitor in parallel with the reference capacitor, or
the reference circuit comprises a reference resistor, the first target state identifying circuit comprises a first target resistor configured, in the first connected state, to be selectively connected in parallel with the reference resistor, the second target resistor configured in the second connected state, to be selectively electrically connected in parallel with the reference resistor and the first target resistor and the second target switch is configured to be controlled to electrically connect the second target resistor in parallel with the reference resistor.

16. The surgical system according to claim 11, wherein
the reference circuit comprises a reference capacitor and the first target state identifying circuit comprises a first target capacitor configured, in the first connected state, to be selectively electrically connected in parallel with the reference capacitor, or
the reference circuit comprises a reference resistor and the first target state identifying circuit comprises a first target resistor configured, in the first connected state, to be selectively electrically connected in parallel with the reference resistor.

17. The surgical system according to claim 12, wherein in an absence of the first target state identifying signal, the baseline signal indicates that the first component is detached from the console.

18. A method comprising:
providing a console comprising:
an electrical isolation device;
a therapy signal generator configured to generate a therapy signal; and
a controller configured to control the therapy signal generator;
providing a first component configured to be directly or indirectly detachably attached to the console, wherein the first component is configured to be driven by the therapy signal to therapeutically affect a biological tissue;

providing a sensor circuit arranged to the console, the sensor circuit comprising:
- a device state signal generation circuit configured to generate a device state signal; and
- a reference circuit configured provide a baseline signal based on the device state signal;

providing a first target state identifying circuit arranged to the first component,
- wherein the first target state identifying circuit is configured to be selectively electrically connected in a first connected state to the sensor circuit, and
- wherein in the first connected state, the first target state identifying circuit is configured to provide a first target state identifying signal based on the device state signal;

enabling the sensor circuit to output a feedback signal based on the baseline signal and the first target state identifying signal; and enabling the controller to control the therapy signal generator based on the feedback signal.

\* \* \* \* \*